(12) United States Patent
Risi

(10) Patent No.: US 7,937,154 B2
(45) Date of Patent: May 3, 2011

(54) PROMOTING CURVATURE AND MAINTAINING ORIENTATION OF AN ELECTRODE CARRIER MEMBER OF A STIMULATING MEDICAL DEVICE

(75) Inventor: Frank Risi, Newtown (AU)

(73) Assignee: Cochlear Limited, Macquarie University, NSW ( * ) Notice: Subject to any disclaimer, the term of this patent is extended or adjusted under 35 U.S.C. 154(b) by 890 days.

(21) Appl. No.: 11/605,951

(22) Filed: Nov. 30, 2006

(65) Prior Publication Data

US 2007/0135884 A1 Jun. 14, 2007

Related U.S. Application Data

(60) Provisional application No. 60/748,217, filed on Dec. 8, 2005, provisional application No. 60/748,273, filed on Dec. 8, 2005, provisional application No. 60/748,274, filed on Dec. 8, 2005, provisional application No. 60/748,314, filed on Dec. 8, 2005.

(51) Int. Cl.
*A61F 2/18* (2006.01)

(52) U.S. Cl. .............................. 607/55; 607/56; 607/57

(58) Field of Classification Search ............... 607/55–57
See application file for complete search history.

(56) References Cited

U.S. PATENT DOCUMENTS

| | | | |
|---|---|---|---|
| 4,261,372 A | 4/1981 | Hansen et al. | |
| 4,532,930 A | 8/1985 | Crosby et al. | |
| 5,167,236 A | 12/1992 | Junker | |
| 5,443,493 A | 8/1995 | Byers et al. | |
| 5,645,585 A * | 7/1997 | Kuzma | 623/10 |
| 5,795,287 A | 8/1998 | Ball et al. | |
| 5,814,095 A | 9/1998 | Muller et al. | |
| 6,070,105 A | 5/2000 | Kuzma | |
| 6,112,124 A | 8/2000 | Loeb | |
| 6,129,753 A | 10/2000 | Kuzma | |
| 6,198,971 B1 | 3/2001 | Leysieffer | |
| 6,259,951 B1 | 7/2001 | Kuzma et al. | |
| 6,537,200 B2 * | 3/2003 | Leysieffer et al. | |
| 6,549,814 B1 | 4/2003 | Strutz et al. | |
| 6,565,503 B2 | 5/2003 | Leysieffer et al. | |

(Continued)

FOREIGN PATENT DOCUMENTS

AU 2002244531 10/2002

(Continued)

OTHER PUBLICATIONS

J Ito, et al. "Tinnitus Suppression by Electrical Stimulation of the Cochlear Wall and by Cochlear Implantation," Department of Otolaryngology, Otsu Red Cross Hospital, Japan, The Laryngoscope vol. 104 (6 Pt. 1). Jun. 1994, pp. 752-754.

(Continued)

*Primary Examiner* — Niketa I Patel
*Assistant Examiner* — Rex Holmes
(74) *Attorney, Agent, or Firm* — Kilpatrick Townsend & Stockton LLP

(57) ABSTRACT

An electrode assembly for use in a prosthetic hearing implant is disclosed, the electrode assembly comprising: an elongate carrier member for implantation into the cochlea, said carrier member having a proximal end adapted to be positioned in a basal region of the cochlea, and a distal end adapted to be positioned toward an apical region of the cochlea, wherein a substantial portion of said carrier member has a fabiform cross section; and a plurality of electrodes disposed along said carrier member.

20 Claims, 6 Drawing Sheets

U.S. PATENT DOCUMENTS

| | | |
|---|---|---|
| 6,575,894 B2 | 6/2003 | Leysieffer et al. |
| 6,697,674 B2 | 2/2004 | Leysieffer et al. |
| 7,194,314 B1 | 3/2007 | Richter et al. |
| 7,315,763 B2 | 1/2008 | Kuzma et al. |
| 2004/0172118 A1* | 9/2004 | Gibson .................. 607/137 |
| 2004/0236390 A1* | 11/2004 | Dadd et al. |
| 2004/0243212 A1* | 12/2004 | Dadd et al. |
| 2005/0080473 A1 | 4/2005 | Gibson et al. |
| 2006/0079950 A1 | 4/2006 | Lehnhardt et al. |
| 2007/0135885 A1* | 6/2007 | Risi |
| 2007/0162098 A1* | 7/2007 | Risi et al. |
| 2007/0282416 A1 | 12/2007 | Gibson et al. |

FOREIGN PATENT DOCUMENTS

| | | | |
|---|---|---|---|
| WO | WO 90/07251 | | 6/1990 |
| WO | 9631087 | | 10/1996 |
| WO | WO-9726943 | * | 7/1997 |
| WO | WO 00/69512 | | 11/2000 |
| WO | WO 02/080817 | | 10/2002 |
| WO | WO-2007027879 | * | 3/2007 |

OTHER PUBLICATIONS

M. Sakajri, et al., "A method for Suppressing Tinnitus by Electrical Stimulation to Cochlea and Remedial Value," Research Institute for Electric Science, Hokkaido University, Sapporo, Japan, Journal of the Acoustical Society of Japan (E), vol. 17, No. 6, pp. 453-455, Nov. 1993.

W. McKerrow, et al., "Tinnitus Suppression by Cochlear Implants," Coleman and Epstein Laboratories Department of Otolaryngology, University of California, San Francisco, The Annals of Otology, Rhinology & Laryngology, Jul. 1991, vol. 100 (7), pp. 552-558.

International Search Report for PCT/AU02/00433, dated May 28, 2002.

AU Examiner's Report for AU 2006202622 dated Apr. 14, 2008.

International Preliminary Examination Report for PCT/AU02/00433 dated Sep. 5, 2002.

Translation of JP Notice of Reasons for Rejection for JP 2002-578856 dated Aug. 5, 2008.

English Translation of Notice of Reasons for Rejection, mailed Jan. 15, 2008 in connection with Japanese Application No. 2002-578856 (3 pages).

* cited by examiner

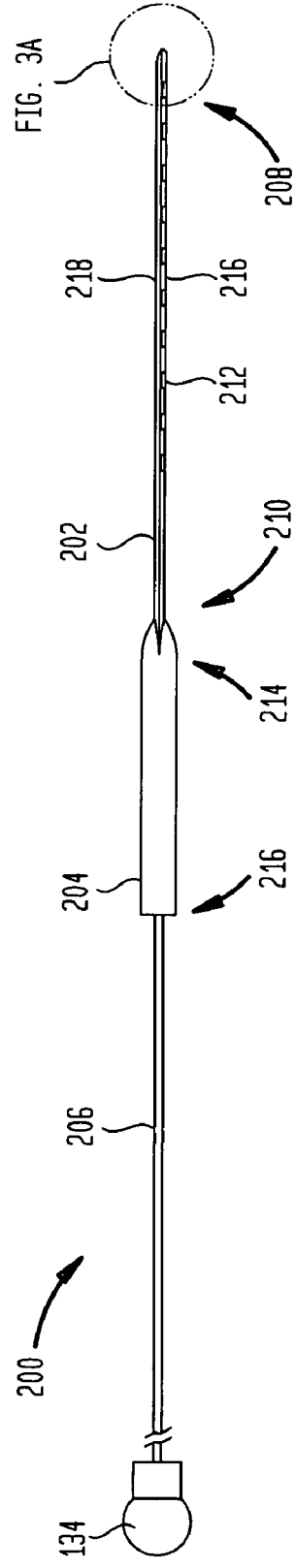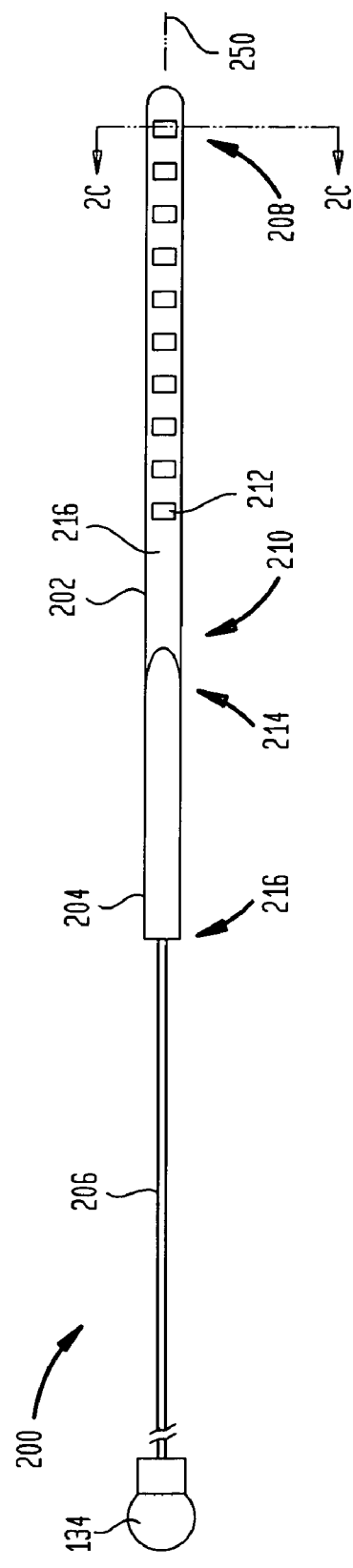

PROMOTING CURVATURE AND MAINTAINING ORIENTATION OF AN ELECTRODE CARRIER MEMBER OF A STIMULATING MEDICAL DEVICE

CROSS-REFERENCE TO RELATED APPLICATIONS

The present application claims priority from U.S. Provisional Patent Application 60/748,217 entitled "Promoting Curvature and Maintaining Orientation In An Electrode Carrier Member Of A Prosthetic Hearing Implant," filed Dec. 8, 2005; U.S. Provisional Patent Application 60/748,273 entitled "Electrode Carrier Member Having An Embedded Stiffener For A Prosthetic Hearing Implant," filed Dec. 8, 2005; U.S. Provisional Patent Application 60/748,274 entitled "Electrode Carrier Member for a Prosthetic Hearing Implant Having Optical Length for Atraumatic Implantation," filed Dec. 8, 2005; and U.S. Provisional Patent Application 60/748,314 entitled "Electrode Carrier Member For A Prosthetic Hearing Implant Having Variable Pitch Electrodes To Facilitate Atraumatic Implantation," filed Dec. 8, 2005, all of which are hereby incorporated by reference herein.

BACKGROUND

1. Field of the Invention

The present invention relates generally to stimulating medical devices and, more particularly, to promoting curvature and maintaining orientation of an electrode carrier member of a stimulating medical device.

2. Related Art

Hearing loss is generally of two types, namely conductive and sensorineural. The treatment of both of types of hearing loss has been quite different, relying on different principles to deliver sound signals to be perceived by the brain as sound. Conductive hearing loss occurs when the normal mechanical pathways for sound to reach the hair cells in the cochlea are impeded, for example, by damage to the ossicles. In such cases, hearing loss is often improved with the use of conventional hearing aids, which amplify the sound so that acoustic information reaches the cochlear hair cells. Such hearing aids utilize acoustic mechanical stimulation, whereby the sound is amplified according to a number of varying techniques, and delivered to the inner ear as mechanical energy. This may be through a column of air to the eardrum, or through direct delivery to the ossicles of the middle ear.

On the other hand, sensorineural hearing loss is due to the absence or destruction of the cochlear hair cells which are needed to transduce acoustic signals into auditory nerve impulses. Individuals suffering from this type of hearing loss are unable to derive any benefit from conventional hearing aid systems regardless of the volume of the acoustic stimulus. This is because the natural mechanisms for transducing sound energy into auditory nerve impulses are either absent or damaged. In such cases, cochlear implants (also referred to as cochlear devices, cochlear prostheses, cochlear implant systems, and the like; simply "cochlear implants" herein) have been developed to provide the sensation of hearing to such individuals. In cochlear implants, electrical stimulation is provided via stimulating electrodes positioned as close as possible to the nerve endings of the auditory nerve, essentially bypassing the hair cells in a normally functioning cochlea. The application of a stimulation pattern to the nerve endings causes impulses to be sent to the brain via the auditory nerve, resulting in the brain perceiving the impulses as sound.

More recently, there has been an increased interest in Electro-Acoustical Stimulation (EAS) in which electrical stimulation of the cochlea is used in conjunction with acoustical stimulation. It is relatively common in hearing impaired individuals to experience sensorineural hearing loss for sounds in the high frequency range, and yet still be able to discern sounds in the middle to low frequency range, through the use of a conventional hearing aid, or naturally. Traditionally, in the majority of such cases, the recipient would only receive treatment to preserve and improve the hearing for the middle to low frequency sounds, most probably via a conventional hearing aid, and little would be done to attempt to restore the hearing loss for the high frequency sounds. This is due to the potential trauma caused by the implantation of an electrode assembly into the cochlea. Only if the individual lost the ability to perceive middle to low frequency sounds would consideration then be given to restoring the hearing loss for the high frequency sounds, in which case a cochlear implant would be considered a possible solution.

SUMMARY

In accordance with one aspect of the present invention, an electrode assembly for use in a prosthetic hearing implant is disclosed, the electrode assembly comprising: an elongate carrier member for implantation into the cochlea, said carrier member having a proximal end adapted to be positioned in a basal region of the cochlea, and a distal end adapted to be positioned toward an apical region of the cochlea, wherein a substantial portion of said carrier member has a fabiform cross section; and a plurality of electrodes disposed along said carrier member.

In another aspect of the invention, an electrode assembly for use in a prosthetic hearing implant is disclosed, the electrode assembly comprising: an elongate carrier member for implantation into the cochlea, said carrier member having a proximal end adapted to be positioned in a basal region of the cochlea, and a distal end adapted to be positioned toward an apical region of the cochlea; and a plurality of electrodes disposed along said carrier member, wherein said carrier member is configured to encourage said carrier member to medially curve about a vertical axis of the carrier member toward the modiolus of the cochlea, to retain its orientation once inserted into the cochlea, and to resist axial rotation.

BRIEF DESCRIPTION OF THE DRAWINGS

Embodiments of the present invention are described herein in conjunction with the accompanying drawings, in which:

FIG. 2A is a side view of an electrode assembly in accordance with one embodiment of the present invention;

FIG. 2B is a top view of the electrode assembly illustrated in FIG. 2A;

DETAILED DESCRIPTION

Embodiments of the present invention are generally directed to an apparatus and method for facilitating implantation of an electrode assembly of a stimulating medical device into a patient (referred to herein as a recipient). Embodiments of the present invention are described below in connection with one type of stimulating medical device, a prosthetic hearing implant and, more specifically, a cochlear implant. Cochlear implants use direct electrical stimulation of auditory nerve cells to bypass absent or defective hair cells that normally transduce acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, the cochlear implant provides stimulation of the cochlear nucleus in the brainstem. Such devices, therefore, are commonly referred to as auditory brainstem implants (ABIs).

Exemplary embodiments of a cochlear implant include a Contour™, Freedom™, Nucleus™ or Cochlear™ implant sold by Cochlear Limited, Australia. Such devices are described in U.S. Pat. Nos. 4,532,930, 6,537,200, 6,565,503, 6,575,894, and 6,697,674, the entire contents and disclosures of which are hereby incorporated by reference herein. It should be understood to those of ordinary skill in the art that embodiments of the present invention may be used in other stimulating medical devices such as neurostimulators, cardiac pacemakers/defibrillators, etc. as well as other medical devices which utilize an elongate carrier member to temporarily or permanently implant, deliver or otherwise introduce a therapeutic agent, sensor, device, etc. into a recipient.

Figure 1:
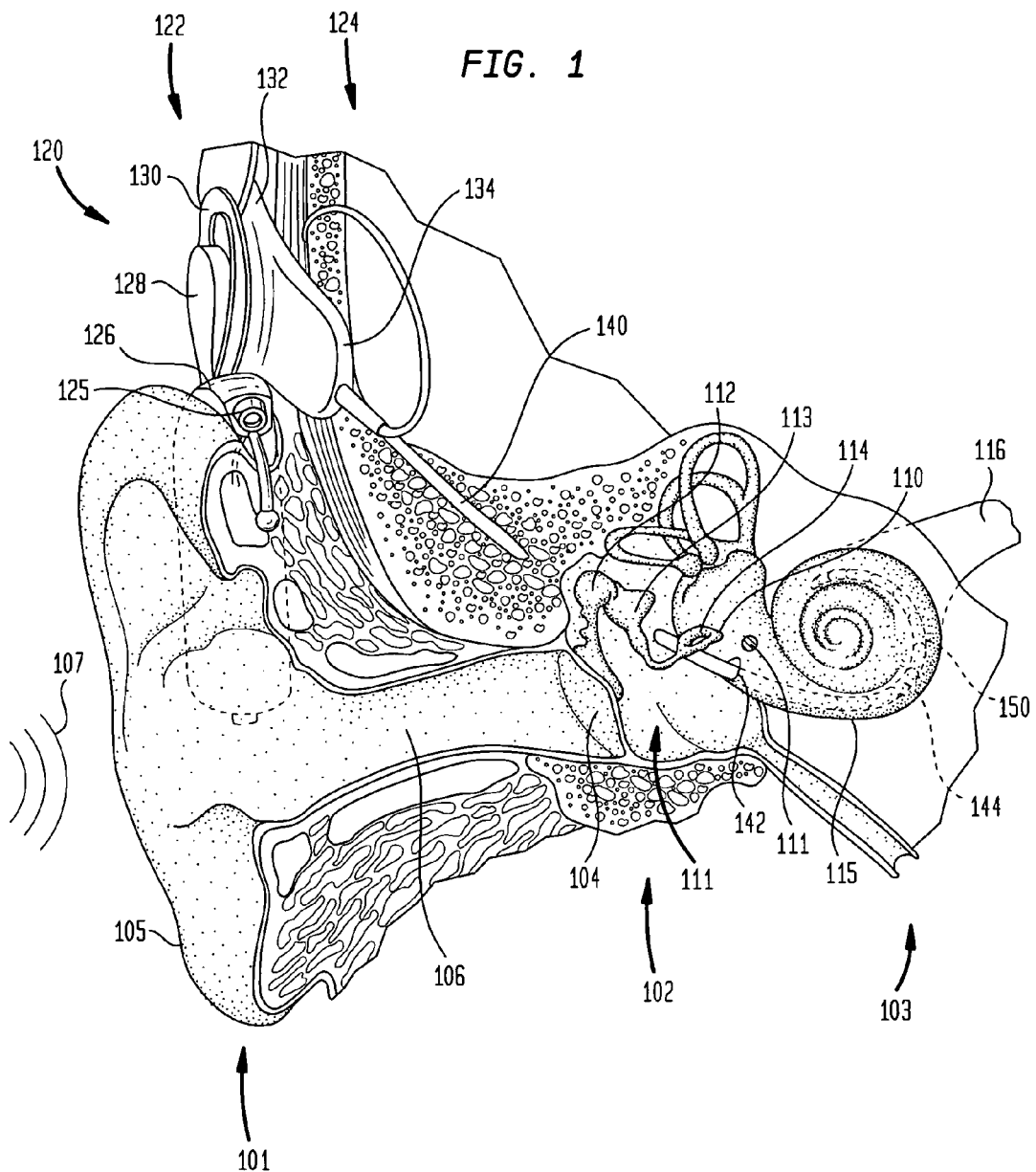
FIG. 1 is a perspective view of an example of an implanted cochlear implant suitable for implementing embodiments of the present invention.

FIG. 1 is a cut-away view of the relevant components of outer ear 101, middle ear 102 and inner ear 103, which are described next below. In a fully functional ear, outer ear 101 comprises an auricle 105 and an ear canal 106. An acoustic pressure or sound wave 107 is collected by auricle 105 and channeled into and through ear canal 106. Disposed across the distal end of ear cannel 106 is a tympanic membrane 104 which vibrates in response to acoustic wave 107. This vibration is coupled to oval window, or fenestra ovalis, 110 through three bones of middle ear 102, collectively referred to as the ossicles 111.

Ossicles 111 comprises the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells (not shown) to auditory nerve 116 and, ultimately, to the brain where they are perceived as sound. In some persons experiencing sensorineural hearing loss, there is an absence or destruction of the hair cells. Cochlear implant 120 is utilized to directly stimulate the ganglion cells to provide a hearing sensation to such persons.

FIG. 1 also shows how cochlear implant 120 is positioned in relation to outer ear 101, middle ear 102 and inner ear 103. Cochlear implant 120 comprises external component assembly 122 which is directly or indirectly attached to the body of the recipient, and an internal component assembly 124 which is temporarily or permanently implanted in the recipient. External assembly 122 comprises microphone 125 for detecting sound which is provided to a behind-the-ear (BTE) speech processing unit 126 that generates coded signals. The coded signals are provided to an external transmitter unit 128, along with power from a power source (not shown) such as a battery. External transmitter unit 128 comprises an external coil 130 and, preferably, a magnet (not shown) secured directly or indirectly in external coil 130.

Internal component assembly 124 comprises an internal receiver unit 132 having an internal coil (not shown) that transcutaneously receives power and coded signals from external assembly 122, and provides such signals to a stimulator unit 134. In response to the coded signals, stimulator 134 applies stimulation signals to cochlea 115 via an implanted electrode assembly 140. Electrode assembly 140 enters cochlea 115 via a cochleostomy 142 or through round window 110, and has an array 144 of one or more electrodes 150 positioned to be substantially aligned with portions of tonotopically-mapped cochlea 115. The delivery of stimulation signals at various locations along cochlea 115 causes a hearing percept representative of the received sound 107.

While cochlear implant 120 is described as having external components, in another embodiment, the controller, including the microphone, speech processor and power supply, may also be implantable. In such embodiments, the controller may be contained within a hermetically sealed housing or the housing used for stimulator unit 134.

Electrode assembly 140 preferably assumes an optimal electrode position in cochlea 115 upon or immediately following implantation into the cochlea. It is also desirable that electrode assembly 140 be configured such that the insertion process causes minimal trauma to the sensitive structures of cochlea 115. Usually electrode assembly 140 is pre-curved, held in a straight configuration at least during the initial stages of the implantation procedure, conforming to the natural shape of the cochlea during and subsequent to implantation.

Figure 2C:
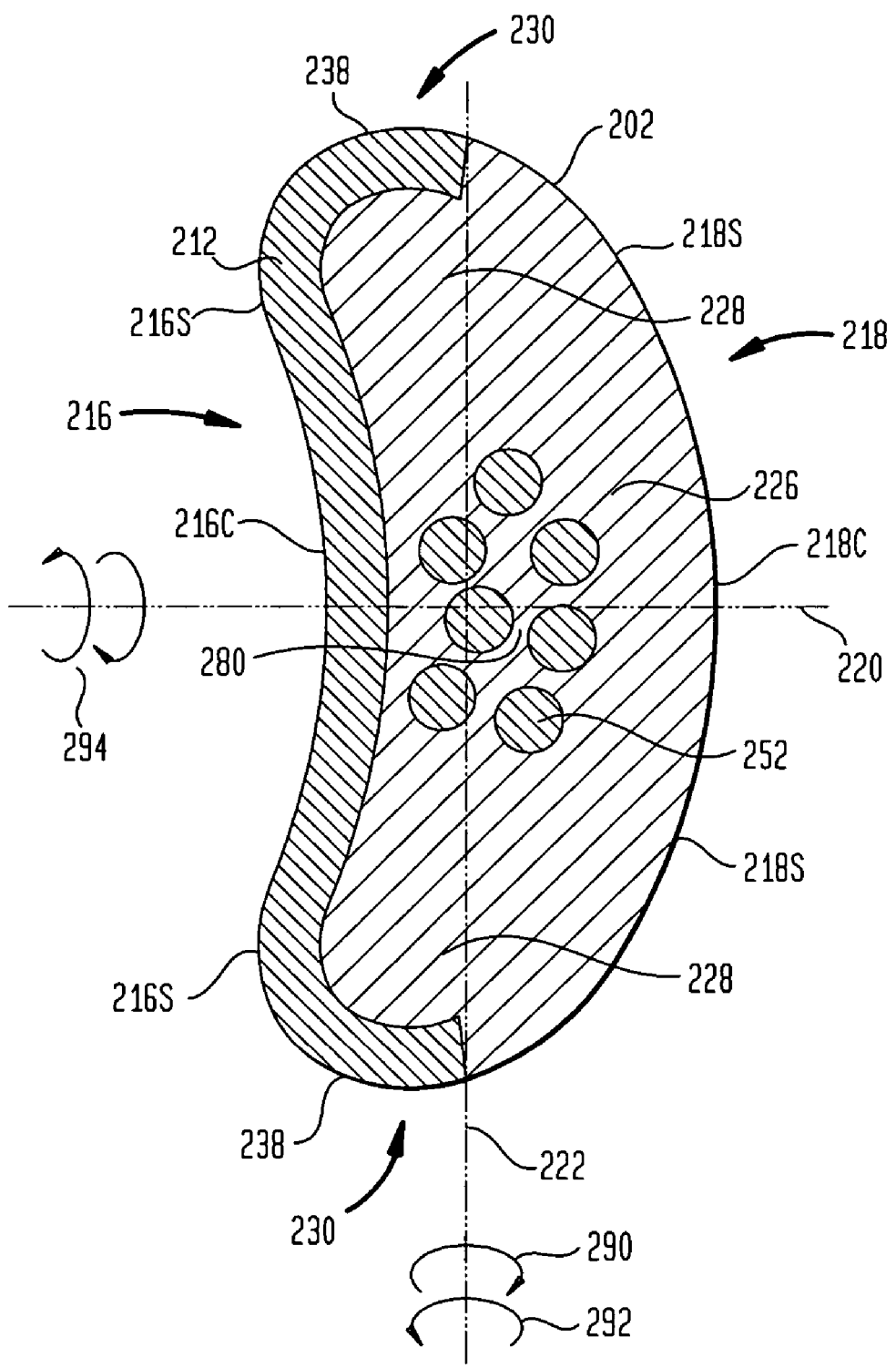
FIG. 2C is a cross-sectional view of one embodiment of the electrode assembly illustrated in FIGS. 2A-2B taken along section line 2C-2C illustrated in FIG. 2B.

FIG. 2A is a side view of an embodiment of electrode assembly 140, referred to herein as electrode assembly 200. FIG. 2B is a top view of electrode assembly 200. FIG. 2C is a cross-sectional view of one embodiment of electrode assembly 200 taken along section line 2C-2C illustrated in FIG. 2B.

Electrode assembly 200 comprises a carrier member 202, a stop member 204 and lead 206. Carrier member 202 has a distal end 208 adapted to be implanted furthest into cochlea 115, and a proximal end 210 connected to a distal end 214 of laterally-extending stop member 204. The opposing proximal end 216 of stop member 204 is connected to lead 206. Lead 206 physically and electrically connects electrode assembly 200 with stimulator unit 134.

When implanted in a recipient, the surface of carrier member 202 which faces the interior of cochlea 115 is referred to herein as the medial surface 216 of carrier member 202. The opposing side of carrier member 202, referred to herein as lateral surface 218, faces the external wall and bony capsule (not shown) of cochlea 115. It should be understood that the terms medial surface, medial direction, and the like, are generally used herein to refer to the surfaces, features and directions toward the center of cochlea 115, while the terms lateral surface, lateral direction, and the like, are generally used herein to refer to surfaces, features and directions toward the exterior of cochlea 115. In addition, a longitudinal axis 250 (FIGS. 2A, 2B) and a horizontal axis 220 and vertical axis 222 (FIG. 2C) are utilized herein to facilitate understanding of the cross-sectional shape and other features of carrier member 202.

A plurality of spaced-apart electrodes 212 are mounted on or in carrier member 202. Electrodes 212 may be disposed in a linear or non-linear array on or in carrier member 202, and may be positioned to align with predetermined regions of tonotopically mapped cochlea 115. In alternative embodiments, electrodes 212 are implemented as described in U.S. Provisional Patent Application 60/748,217, 60/748,273 and 60/748,314, hereby incorporated by reference herein.

As shown in FIG. 2C, electrodes 212 are, in this embodiment, half-band electrodes disposed on medial surface 216 of carrier member 202. It should be appreciated, however, that any electrodes now or later developed suitable for a particular application may be used in alternative embodiments of the invention. For example, in one alternative embodiment, electrodes 212 are banded electrodes extending substantially around carrier member 202. In another alternative embodiment, electrodes 212 do not laterally extend to or around the edges of carrier member 202.

Typically, each electrode 212 is arranged such that its exposed surface is generally parallel with vertical axis 222 of carrier member 202, as depicted in FIG. 2C. It should be appreciated, however, that other electrode positions and orientations may be implemented in alternative embodiments. It should further be appreciated that the quantity of electrodes 212 may vary from as few as one or two to as many as twenty-four or more.

In certain embodiments, at least one electrode 212 has a surface that is at least adjacent medial surface 216 of carrier member 202. Preferably, one or more electrodes 212 has a surface that is collocated with medial surface 216 of carrier member 202, as shown in FIG. 2C. In other embodiments, the surfaces of electrodes 212 are raised above or recessed into medial surface 216 of carrier member 202.

Electrodes 212 may be manufactured from a biocompatible conductive material such as platinum, although other materials or combinations of materials may be used. Alternatively, electrodes 212 may be coated with a biocompatible covering that does not interfere with transfer of stimulation signals to cochlea 115.

Each electrode 212 is electrically connected to at least one multi- or single-filament wire 252 that is embedded within flexible carrier member 202, stop member 204 and lead 206. In one embodiment, wires 252 are embedded in the volumetric core 280 of carrier member 202. In an alternative embodiment, wires 252 may be located at or near surfaces 216 and/or 218 of carrier member 202. In other embodiments, wires 252 are embedded in different regions of carrier member 202 to facilitate curvature and/or to maintain orientation of carrier member 202 once it is implanted. It is through wires 252 that stimulator unit 134 (FIG. 1) provides electrical stimuli to selected electrodes 212. In one embodiment, wires 252 are connected to electrodes 212 by welding, although any suitable techniques now or later developed to electrically connect electrodes 212 to wires 252 may be used.

It should be appreciated that the quantity of wires 252 connected to each electrode 212 may vary. For example, in one alternative embodiment, at least two electrically conducting wires 252 are connected to electrode 212. It should also be appreciated that suitable transmission means other than filament wires may be used to communicably couple receiver/stimulator unit 134 and electrodes 212. For example, semiconductor or wireless technologies may be used.

In one embodiment, lead 206 (FIGS. 2A, 2B) may extend from carrier member 202 to stimulator 134 or at least the housing thereof. In one particular embodiment, lead 206 is continuous with no electrical connectors, at least external the housing of stimulator unit 134; that is, there are no external connectors required to electrically connect electrode assembly 200 to stimulator 134. One advantage of this arrangement is that there is no need for a surgeon implanting electrode assembly 200 to make a requisite electrical connection between wires 252 extending from electrodes 212 and stimulator 134. Stimulator 134 is preferably encased within an implantable housing that is implantable within the recipient. The housing for stimulator 134 is preferably implantable within a recess in the bone behind the ear posterior to the mastoid.

Carrier member 202 has a fabiform, i.e. bean-shape, cross section as shown in FIG. 2C. Carrier member 202 comprises an elongate central region 226 and unitary or integral side regions 228. In the embodiment shown in FIG. 2C, side regions 228 vertically extend along vertical axis 222 from opposing sides of central region 226. In addition, side regions 228 are substantially uniform in dimensions and orientation. As such, this embodiment of carrier member 202 is substantially symmetrical about horizontal axis 220.

The surface tangent of medial surface 216, lateral surface 218 and surfaces 230 of side regions 228 change gradually from one surface to an adjacent surface to form a smooth, contiguous carrier member surface with no sharp or locally discrete edges or corners. Each of these surfaces 216, 218 and 230 are described in detail next below.

The portion of lateral surface 218 at central region 226, referred to as lateral surface 218C, has a convex shape with a substantially consistent radius of curvature. Similarly, the shape of lateral surface 218 at side regions 228, referred to as lateral surfaces 218S, are similarly convex and also have a consistent radius of curvature. As shown in FIG. 2C, the radius of curvature of central and side region lateral surfaces 218C, 218S is substantially the same, resulting in a carrier member lateral surface 218 that has a substantially consistent radius across the entire lateral surface.

The portion of medial surface 216 at central region 226, referred to as medial surface 216C, is a concave surface. The portion of medial surface 216 at side regions 228, referred to herein as medial surfaces 216S, are convex. The surface slope of carrier member 202 transitions gradually from medial surfaces 216S of side regions 228 to medial surface 216C at central region 226, as shown in FIG. 2C.

It should be appreciated that the radius of curvature of concave surface 216C and convex surfaces 216S may be different in alternative embodiments depending, for example, on the relative thickness of central region 226 and side regions 228, the desired rate of change of the surface slope across medial surface 216, and the desired proximity of electrodes 212 disposed on medial surface 216.

Side surfaces 230 comprise convex surface 238 between and contiguous with convex surfaces 216S and 218S. In other words, side regions 228 each have convex surface 238 that provides a transition between opposing medial and lateral surfaces 216S, 218S. As shown in FIG. 2C, side surfaces 230 have no sharp edges. Rather, side surfaces 230 have a minimum radius of curvature which is greater than zero to provide smooth, curved ends on carrier member 202. This reduces the likelihood that side surfaces 230 of carrier member 202 may damage cochlea 115 or its surrounding anatomy during or after implantation.

In certain embodiments, carrier member 202 has a minimized volume to facilitate implantation. This reduced cross-sectional volume may cause conventional carrier members to bend in unintentional directions during implantation. To prevent this from occurring, embodiments of carrier member 202 have longitudinally-extending structural support as described in International Application PCT/US06/34010 entitled, "Elongate Implantable Carrier Member Having An Embedded Stiffener," and filed Aug. 31, 2006; U.S. patent application entitled "Prosthetic Hearing Implant Electrode Assembly Having Optimal Length for Atraumatic Implantation," filed concurrently U.S. application Ser. No. 11/605,952 (US Publication 2007/0162098 A1); and U.S. patent application entitled "Flexible Electrode Assembly Having Variable Pitch Electrodes for a Stimulating Medical Device," filed concurrently under U.S. application Ser. No. 11/605,960 (US Publication 2007/0135885 A1) all of which are hereby incorporated by reference herein.

In other embodiments, such support is additionally or alternatively provided by the distribution of embedded wires 252. In alternative embodiments, such structural support may be provided by other materials embedded in carrier member 202, by varying the density or materials used to form carrier member 202, etc. Such embodiments provide for establishing selective flexibility along carrier member 202 to, for example, increase the "pushability" and "trackability" of carrier member 202 during insertion. It should be appreciated, however, that such selective flexibility should not prevent carrier member 202 from being able to coil or turn 290, 292 about vertical axis 222 so that it may follow the contour of cochlea 115 during implantation. In other words, such structural support serves to increase the longitudinal rigidity and, perhaps, limit curving 294 about horizontal axis 220 while permitting curving 290 about vertical axis 222. In one embodiment, the thickness of carrier member 202 is substantially constant for at least a majority of its length. In other embodiments, the thickness may be longitudinally tapered as described in the above-noted US Provisional Applications.

This fabiform cross-section of carrier member 202 is continuous along axial direction 250 of electrode assembly 200 and may be achieved by any manufacturing process now or later developed. In one embodiment, carrier member 202 is formed by excluding material (either or both silicone carrier and platinum contacts) from carrier member 202.

The fabiform cross-section encourages carrier member 202 to curve or coil about a vertical axis 222; that is, curving medially toward the modiolus of cochlea 115. This arrangement provides an electrode carrier member 202 that retains its natural stiffness, however, when encouraged (such as when a straight electrode assembly 200 makes contact with a lateral wall of cochlea 115) the electrode assembly 200 will more easily and naturally curve in the desired direction (medially) thus reducing impact and friction forces. This is because there is less mass of material created by the concave cross-section, the resistance to coiling toward a convex surface, and/or other features.

An advantage of the noted fabiform cross-sectional shape of carrier member 202 over conventional carrier members is a reduction of the risk of causing residual hearing loss upon insertion of electrode assembly 200. Hence, this is particularly suited for straight electrode assemblies that are intended to preserve residual hearing. Straight electrode assemblies rely on the fragile cochlea structures to guide and curve the carrier member as it progresses along the lateral wall of cochlea 115. Being able to reduce the forces on these structures provides significant benefits. However, the fabiform profile can be used for non-EAS applications as well.

Additionally, electrode assembly 200 will tend to retain its orientation once inserted into cochlea 115. Having a non-symmetrical cross-section also ensures that some stiffness is maintained perpendicular to the curvature, therefore ensuring that electrode assembly 200 does not twist or rotate axially, ensuring electrodes 212 are always directed toward the nerve. This is similar to say a tape measure whose curvature helps maintain orientation whilst still allowing it to be retracted and curled into the housing.

Maintaining orientation allows the placement of electrodes 212 on medial side 216 only, so that lateral side 218 of carrier member 202 can be a continuous smooth silicone surface, further reducing friction.

A further alternative arrangement is for concave surface 216C to be parabolic, thereby providing additional benefits as far as focusing the charge from each electrode 212. This may improve stimulation specificity.

Another advantage of certain aspects and embodiments of the present invention is that elongate carrier member 202 facilitates atraumatic implantation through the round window membrane 110. Creating cochleostomy 142 has the potential of inducing trauma as a result of drilling the cochlea bone. For example, the drilling may cause bone dust to enter cochlea 115, mechanical trauma, suction of perilymph, etc. In addition, there is a likelihood that the location of cochleostomy 142 is less than optimal for atraumatic insertion of an electrode assembly carrier member. In contrast, implantation through round window 111 guarantees a proper positioning of the electrode assembly in the scala tympani, and requires no drilling. However the anatomy of round window 111 requires utilizing either a very thin carrier member (<0.5 mm) or a carrier member of the present invention having a kidney bean cross-sectional shape to allow insertion through a slit in round window membrane 111 (parallel to lateral vertical axis 222), whilst still leaving the round window intact and mobile.

Figure 3A:
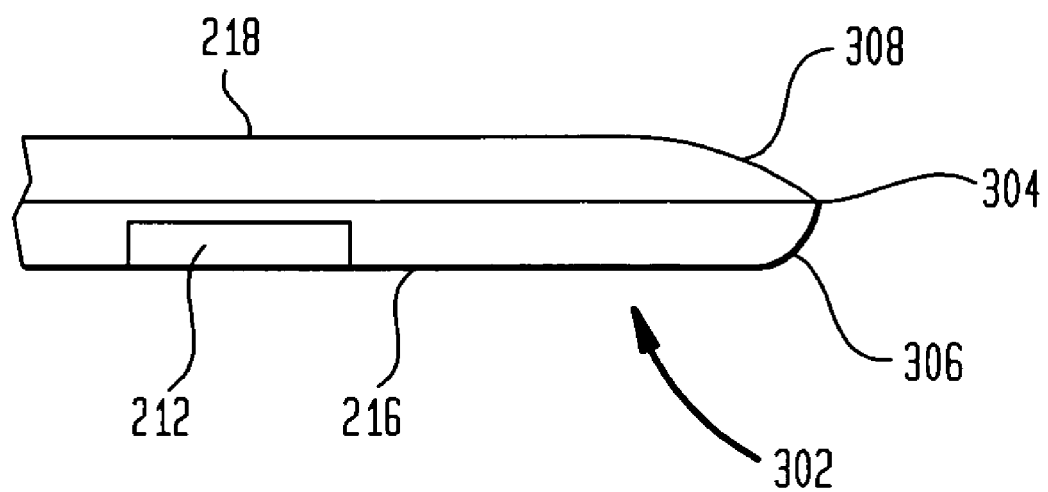
FIG. 3A is an enlarged view of one embodiment of a tip region of the electrode assembly illustrated in FIG. 2A.

FIG. 3A is an enlarged view of one embodiment of a tip region of the electrode assembly illustrated in FIG. 2A, referred to herein as tip region 302. In certain embodiments, a longitudinally-tapered tip region is formed at distal end 208 of carrier member 202. In one embodiment, the thickness of carrier member 202 gradually tapers toward distal end 208 in tip region 302. Tip region 302 facilitates the insertion of carrier member 202 into a recipient's cochlea. In one embodiment, tip region 302 comprises a taper 308 which slopes from lateral surface 218 rearward and inward toward medial surface 216. Such a tapered tip region 208 aids the coiling of carrier member 202 during implantation and further helps prevent damage to the delicate structures of the cochlea. In alternative embodiments, tip region 302 is a rounded surface 306 extending from medial surface 216 to front edge 304, and a rounded surface 308 extending from lateral surface 218 to front edge 304. Thus, in this embodiment, both sides of carrier member 202 are tapered, with each having a different radius of curvature.

Figure 3B:
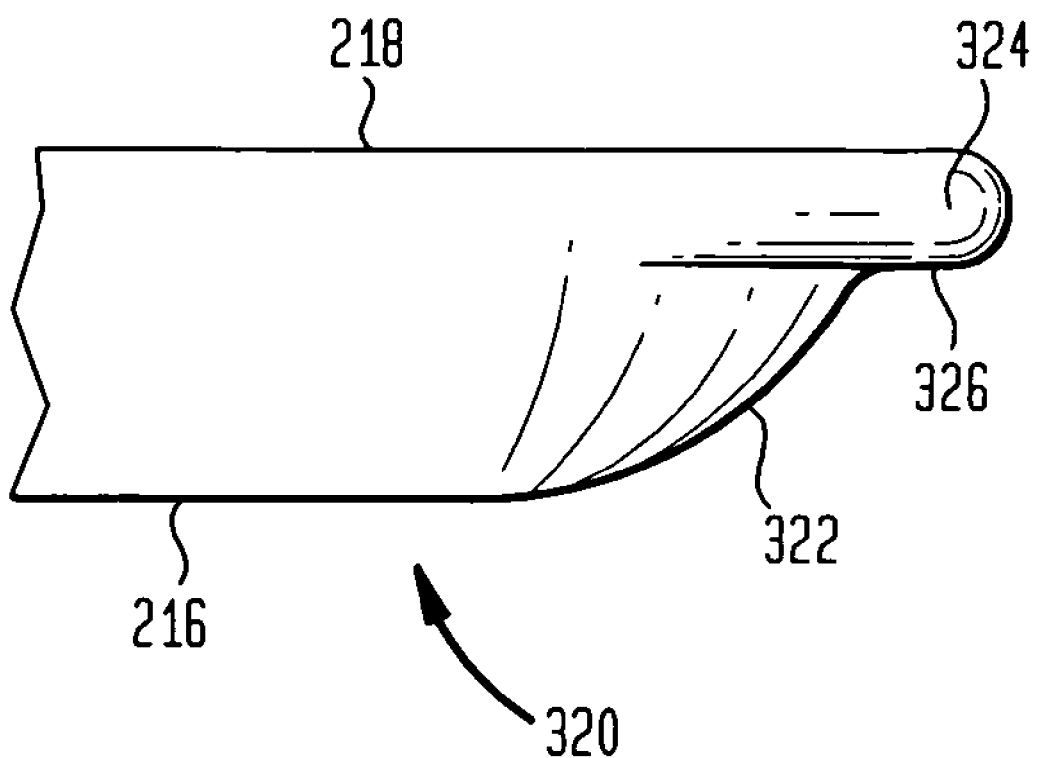
FIG. 3B is an alternative embodiment of a tip region of the electrode assembly illustrated in FIG. 2A.

An alternative embodiment of a tip region of electrode assembly 200 is illustrated in FIG. 3B, referred to herein as tip region 320. Here, tip region 320 has a bottle-nose configuration. That is, at tip region 320 medial surface 216 is curved 322 toward lateral surface 218. An extension 324 extends beyond curvature 322 to form a plateau 326. The surface of extension 324 opposing plateau 326 is, in this embodiment, planar and contiguous with lateral surface 218. The leading edge of extension 324 is curved or rounded to provide a blunt leading surface on a carrier member 202 implanting tip region 320. The radius of curvature of curved surface 350 preferably transitions gradual from medial surface 216 and plateau 326 to avoid abrasions.

Figure 3C:
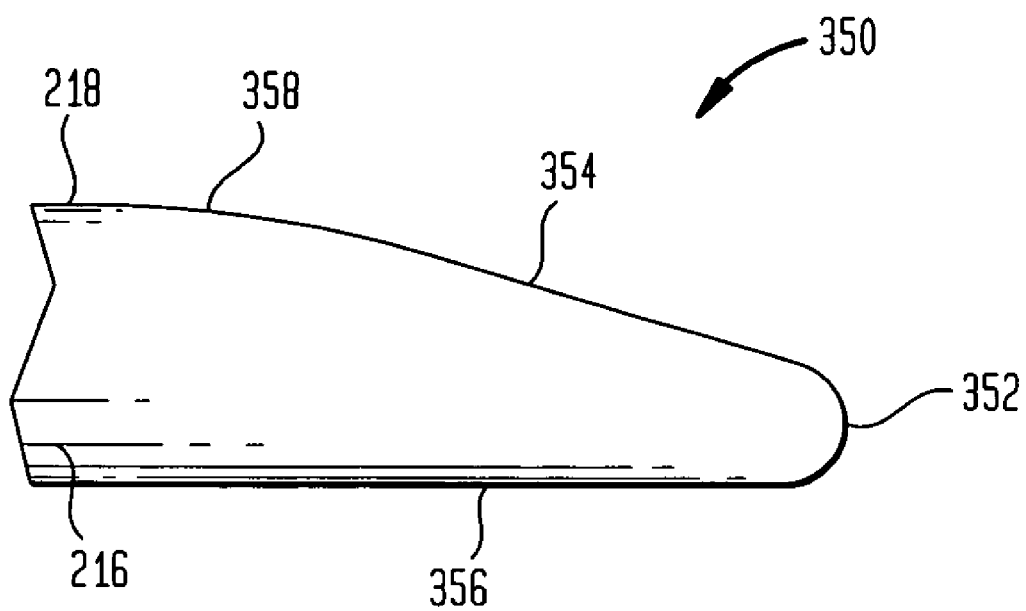
FIG. 3C is an alternative embodiment of a tip region of the electrode assembly illustrated in FIG. 2A.

FIG. 3C is a side view of another embodiment of a tip region of carrier member 202, referred to herein as tip region 350. Tip region 350 is configured to facilitate coiling of carrier member 202 around vertical axis 222 toward medial surface 216, as well as to minimize trauma, when carrier member 202 is inserted through round window 110 of cochlea 115.

Tip region 350 tapers 354 toward a narrower distal end 352 on lateral surface 218 taper 354 begins at a curvature 358 that has a radius of curvature that substantially matches the curvature of the lateral wall of cochlea 115. In this exemplary embodiment, the opposing side 356 is substantially planar and is continuous with medial surface 216.

Surfaces 354 and 356 merge at distal end 352, as shown in FIG. 3C. Distal end 352 has a radius of curvature that is substantially small such that the diameter defined by such radius of curvature is substantially less than the thickness or diameter 360 of the body of carrier member 202.

Profiled tip region 350 reduces the contact area with the spiral ligament and also increase the safe/atraumatic insertion angle range. Additionally tip region 350 has been shown to more easily be inserted through the round window 111 as it acts as a wedge, opening up the slit membrane as carrier member 202 is inserted. That is, after the membrane forming round window 111 has been slit the surgeon must open the slit to some extent to pass carrier member 202 through. If a conventional blunt electrode is used, the force required to pass it through the slit may be greater than the force required to buckle electrode assembly 200. In contrast, a carrier member 202 having a profiled tip 350 reduces the force required to introduce electrode assembly 200 through round window 110, allowing the use of a more flexible electrode assembly 200.

In alternative embodiments, the tip region of carrier member 202 may be as described in U.S. patent application Ser. No. 10/825,358 (Now Abandoned), which is hereby incorporated by reference herein.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

All documents, patents, journal articles and other materials cited in the present application are hereby incorporated by reference, herein.

What is claimed is:

1. An electrode assembly for use in a prosthetic hearing implant, comprising:
   an elongate carrier member for implantation into a cochlea, said carrier member having a proximal end adapted to be positioned in a basal region of the cochlea, and a distal end adapted to be positioned toward an apical region of the cochlea, wherein a substantial portion of said carrier member has a fabiform cross section in which a lateral surface of said fabiform shape is convex and a central portion of a medial surface of said fabiform shape is concave; and
   a plurality of electrodes disposed along said carrier member.

2. The electrode assembly of claim 1, wherein said medial and lateral surfaces are opposing longitudinal surfaces configured such that, when said carrier member is implanted, said medial surface faces toward the center of the cochlea and said lateral surface faces toward the exterior of the cochlea, wherein said electrode assembly further comprises:
   a tapered tip region comprising a first rounded surface extending from said medial surface to a distal end of said tip region, and a second rounded surface extending from said lateral surface to said tip region, wherein a radius of curvature of the first rounded surface is greater than a radius of curvature of the second rounded surface.

3. The electrode assembly of claim 1, wherein said medial and lateral surfaces are opposing longitudinal surfaces configured such that, when said carrier member is implanted, said medial surface faces toward the center of the cochlea and said lateral surface faces toward the exterior of the cochlea, wherein said electrode assembly further comprises:
   a tapered tip region disposed at said distal end of said carrier member, wherein said tip region comprises a distal end having a radius of curvature, wherein said tip region comprises a sloping surface that slopes from said curved distal end toward said proximal end of said carrier member, and slopes upward from said curved distal end toward said lateral surface.

4. The electrode assembly of claim 3, wherein said tip region further comprises a convex surface disposed between said sloping surface and said lateral surface, wherein said convex surface has a radius of curvature that is configured to substantially match a curvature of a lateral wall of the cochlea.

5. The electrode assembly of claim 1, wherein said medial and lateral surfaces are opposing longitudinal surfaces configured such that, when said carrier member is implanted, said medial surface faces toward the center of the cochlea and said lateral surface faces toward the exterior of the cochlea, wherein said electrode assembly further comprises:
   a tapered tip region disposed at said distal end of said carrier member, wherein said tip region has a bottle-nose configuration.

6. The electrode assembly of claim 1, further comprising:
   a laterally-extending collar member connected to said proximal end of said carrier member and configured to abut the cochlea when said carrier member is implanted at a maximum insertion depth, and to prevent further insertion of said carrier member into the cochlea beyond said maximum insertion depth.

7. The electrode assembly of claim 1, wherein said carrier member is longitudinally-tapered, wherein said proximal end of said carrier member has greater dimensions than said distal end of said carrier member.

8. The electrode assembly of claim 6, wherein, in one or more radial directions, said collar member has a diameter greater than a diameter of said carrier member.

9. The electrode assembly of claim 6, further comprising:
   an elongate lead connected to said proximal end of said carrier member, said lead physically and electrically connecting said electrode assembly to an implantable stimulator unit.

10. The electrode assembly of claim 9, wherein said lead is continuous with no intermediate electrical connectors between said electrode assembly and the stimulator unit.

11. The electrode assembly of claim 1, wherein each of said plurality of electrodes is electrically connected to at least one multi- or single-filament wire embedded within said carrier member.

12. The electrode assembly of claim 11, wherein said wires are embedded in a volumetric core of said carrier member.

13. The electrode assembly of claim 11, wherein said wires are located in different regions of said carrier member to facilitate curvature or to maintain orientation of said carrier member once said carrier member is implanted.

14. The electrode assembly of claim 1, wherein said medial and lateral surfaces are opposing longitudinal surfaces configured such that, when said carrier member is implanted, said medial surface faces toward the center of the cochlea and said lateral surface faces toward the exterior of the cochlea,
   wherein at least one of said plurality of electrodes is a half-band electrode disposed on said medial surface of said carrier member.

15. The electrode assembly of claim 14, wherein each of said plurality of electrodes has a surface that is collocated with said medial surface of said carrier member.

16. An electrode assembly for use in a prosthetic hearing implant, comprising:

an elongate carrier member for implantation into a cochlea, said carrier member having a proximal end adapted to be positioned in a basal region of the cochlea, a distal end adapted to be positioned toward an apical region of the cochlea, a convex lateral surface, and a medial surface having a concave central portion; and a plurality of electrodes disposed along said carrier member, wherein said carrier member comprises a cross-sectional shape configured to encourage said carrier member to medially curve about a vertical axis of the carrier member toward the modiolus of the cochlea, to retain its orientation once inserted into the cochlea, and to resist axial rotation.

17. The electrode assembly of claim 16, wherein said carrier member is configured to be atraumatically implanted through a slit in the round window membrane of the cochlea without adversely affecting the operability of the round window.

18. The electrode assembly of claim 16, wherein said electrodes are located only on said medial side, and wherein said lateral side is formed of a continuous smooth silicone surface.

19. The electrode assembly of claim 16, wherein said plurality of electrodes are positioned along said carrier member so as to align with predetermined regions of a tonotopically mapped cochlea when said carrier member is implanted.

20. The electrode assembly of claim 16, wherein said medial and lateral surface are opposing longitudinal surfaces configured such that, when said carrier member is implanted, said medial surface faces toward the center of the cochlea and said lateral surface faces toward the exterior of the cochlea, wherein at least one of said plurality of electrodes has a surface that is collocated with said medial surface of said carrier member.

* * * * *